US012740974B2

(12) United States Patent
Lee et al.

(10) Patent No.: US 12,740,974 B2
(45) Date of Patent: Sep. 22, 2026

(54) ORALLY-DISINTEGRATING FILM COMPRISING NARATRIPTAN

(71) Applicant: CMG PHARMACEUTICAL CO., LTD., Seoul (KR)

(72) Inventors: Dayeon Lee, Seoul (KR); Hyunjun Jeong, Suwon-si (KR); Kyoungtae Nam, Suwon-si (KR); Taehee Han, Seoul (KR)

(73) Assignee: CMG PHARMACEUTICAL CO., LTD., Seoul (KR)

( * ) Notice: Subject to any disclaimer, the term of this patent is extended or adjusted under 35 U.S.C. 154(b) by 417 days.

(21) Appl. No.: 18/337,732

(22) Filed: Jun. 20, 2023

(65) Prior Publication Data

US 2023/0330079 A1 Oct. 19, 2023

Related U.S. Application Data

(63) Continuation of application No. PCT/KR2021/017886, filed on Nov. 30, 2021.

(30) Foreign Application Priority Data

Dec. 21, 2020 (KR) ........................ 10-2020-0180144

(51) Int. Cl.

| | |
|---|---|
| ***A61K 31/454*** | (2006.01) |
| ***A61K 9/00*** | (2006.01) |
| ***A61K 47/12*** | (2006.01) |
| ***A61K 47/38*** | (2006.01) |

(52) U.S. Cl.

CPC ............ *A61K 31/454* (2013.01); *A61K 9/006* (2013.01); *A61K 47/12* (2013.01); *A61K 47/38* (2013.01)

(58) Field of Classification Search

None

See application file for complete search history.

(56) References Cited

U.S. PATENT DOCUMENTS

| | | | | |
|---|---|---|---|---|
| 2009/0004254 A1* | 1/2009 | Maibach | .................. | A61P 1/08 424/444 |
| 2015/0038594 A1* | 2/2015 | Borges | .................. | A61K 47/14 514/772.2 |

FOREIGN PATENT DOCUMENTS

| | | | | |
|---|---|---|---|---|
| JP | 2009-501751 A | 1/2009 | | |
| JP | 2012-528854 A | 11/2012 | | |
| JP | 2015-218153 A | 12/2015 | | |
| JP | 2020-500220 A | 1/2020 | | |
| KR | 10-2001-0107754 A | 12/2001 | | |
| KR | 10-2005-0048056 A | 5/2005 | | |
| KR | 10-2009-0080037 A | 7/2009 | | |
| KR | 10-2010-0138768 A | 12/2010 | | |
| KR | 10-2012-0100683 A | 9/2012 | | |
| KR | 10-1303479 B1 | 9/2013 | | |
| KR | 10-1626873 B1 | 6/2016 | | |
| KR | 10-2019-0105569 A | 9/2019 | | |
| WO | WO-2018091473 A1 * | 5/2018 | ............. | A61K 9/006 |

OTHER PUBLICATIONS

Seeburger, et. al. Rizatriptan for Treatment of Acute Migraine in Patients Taking Topiramate for Migraine Prophylaxis; Headache, 52, p. 57-67 (Year: 2012).*

Bhikshapathi et al., "Preparation and Evaluation of Fast Dissolving Oral Film Containing Naratriptan HCI." Am. J. PharmaTech Res., 2014, 4(2), 799-812.

Krishna et al., "Preparation and Optimization of Fast Dissolving Film of Naratriptan Hydrochloride," Recent Patents on Drug Delivery and Formulation, 2017, 11(2), 124-31.

* cited by examiner

*Primary Examiner* — Ali Soroush
*Assistant Examiner* — Elizabeth Anne Meyers
(74) *Attorney, Agent, or Firm* — United One Law Group LLC; Kongsik Kim; Jhongwoo Peck

(57) ABSTRACT

An orally dissolving film formulation comprises: naratriptan, sumatriptan, eletriptan, frovatriptan, almotriptan, zolmitriptan, rizatriptan or a salt thereof as an active ingredient; and a buffer. A method for preparing an orally dissolving film formulation comprises adding a buffer to a solvent to adjust pH of the mixed solution, adding an active ingredient, a film forming agent and an additive, and applying heat, and drying to prepare a thin film.

13 Claims, 11 Drawing Sheets

ORALLY-DISINTEGRATING FILM COMPRISING NARATRIPTAN

CROSS-REFERENCE TO RELATED APPLICATIONS

This application is a Continuation of International Application No. PCT/KR2021/017886 filed on Nov. 30, 2021, which claims priority from Korean Patent Application No. 10-2020-0180144, filed on Dec. 21, 2020. The aforementioned applications are incorporated herein by reference in their entireties.

TECHNICAL FIELD

The present invention relates to an orally dissolving film formulation comprising naratriptan or a pharmaceutically acceptable salt thereof. Specifically, the present invention relates to an orally dissolving film formulation comprising naratriptan or a pharmaceutically acceptable salt thereof and a buffer.

RELATED ART

Migraine is a type of headache caused by dysfunction of the brain, cranial nerves, and cerebral vessels. It occurs at any age, but it first occurs between the ages of 10s and 20s, and is most common in those in their 40s and 50s. In Korea, it is a very common disease affecting 9% of women and 3% of men.

The mechanism by which migraine occurs is not yet clearly understood. However, it is thought that neurotransmitters such as serotonin, dopamine, and glutamate play an important role. Therefore, a triptan-based compound that specifically acts on serotonin receptors is attracting attention.

The triptan-based compound selectively binds to the serotonin 5-HT1B and 5-HT1D receptors in the cranial vessels to constrict cerebral vessels. Subsequently, it also acts to inhibit the release of pro-inflammatory neuropeptides.

A typical triptan-based compound is an oral tablet, which is taken with water, but it is difficult for patients or children to swallow the drug. In order to overcome these problems, recently, an orally disintegrating tablet (ODT), which can be swallowed by rapidly disintegrating in the oral cavity without water, has been developed (Korean Patent Registration No. 10-1626873, Korean Patent Application Publication No. 10-2001-0107754). However, an orally disintegrating tablet is easier to be taken than a tablet, but is easily broken due to its low hardness, and is not easy to carry due to the increase in volume due to excipients. In addition, the use of a large amount of excipients may give a foreign body sensation in the oral cavity.

Film-type preparations that compensate for the disadvantages of these orally disintegrating tablets and have reduced volume and amount of excipients have recently been developed. The orally dissolving film (ODF) is thin and has a flexible shape, so it is easy to carry and does not break easily. In addition, since the disintegration time is short due to the large surface area in the form of a film, it blocks the foreign body sensation in the oral cavity and masks the bitter taste of the drug.

However, in the case of an orally dissolving film, the mixture of a drug, a film forming agent and other additives must maintain a certain viscosity. Since the amount of water or organic solvent is limited in order to maintain viscosity, some poorly soluble drugs or water-insoluble drugs are not suitable for an orally dissolving film. In particular, an active ingredient such as triptans is unstable to temperature and humidity, making it difficult to prepare an orally dissolving film formulation.

According, the present inventors have developed an excellent film formulation in which an active ingredient such as triptans is stably maintained, an active ingredient is rapidly eluted during oral dissolution to exert medicinal effects, and side effects such as precipitation do not occur even during storage of the film formulation. Based on the above, the present inventors completed the present invention.

SUMMARY

The present invention relates to an orally dissolving film formulation that can be taken without water compared to general formulations for oral administration and thus enhances the convenience of taking the medicine. Moreover, an object of the present invention is to provide an orally dissolving film formulation with improved pharmaceutical properties such as stability and dissolution rate compared to previously known orally dissolving formulations.

In order to achieve the above object, the present invention provides an orally dissolving film formulation comprising naratriptan, sumatriptan, eletriptan, frovatriptan, almotriptan, zolmitriptan, rizatriptan or a salt thereof as an active ingredient, and a buffer.

In one embodiment, it may be an orally dissolving film formulation, wherein the active ingredient is naratriptan.

In one embodiment, the formulation may be an orally dissolving film formulation, wherein the active ingredient is dissolved by 85% or more, more preferably by 90% or more, and most preferably by 95% or more within 5 minutes during a dissolution test.

The buffer may be citric acid, sodium citrate, potassium citrate, acetic acid, sodium acetate, malic acid, sodium glutamate, glycine, sodium carbonate, maleic acid, sodium lactate, sodium dihydrogen phosphate, sodium monohydrogen phosphate, potassium dihydrogen phosphate, potassium monohydrogen phosphate or a mixture thereof, but is not limited thereto.

In one embodiment, the buffer may comprise a mixture of citric acid and sodium citrate, and may comprise 0.1 to 2.0% by weight of the buffer based on the total weight of the film solids.

In one embodiment, the buffer may comprise 0.1 to 2.0% by weight of sodium citrate and 0.01 to 0.1% by weight of citric acid based on the total weight of the film solids.

The "total weight of the film solids" refers to the total weight of solid components such as a surfactant, a binder, a plasticizer, a disintegrant, a sweetener, a flavoring agent and a coloring agent, excluding solvents in the film formulation.

The present invention provides an orally dissolving film formulation, wherein the content of the total related substances is less than 3%, more preferably less than 2%, and most preferably less than 1% after 6 months during an accelerated stability test.

In one embodiment, the formulation may further comprise a film forming agent. The film forming agent may be pullulan, sodium alginate, hydroxypropyl cellulose, hydroxypropyl methyl cellulose or a mixture thereof, and preferably hydroxypropyl methyl cellulose, but is not limited thereto.

In addition, the present invention provides a method for preparing an orally dissolving film formulation comprising naratriptan, sumatriptan, eletriptan, frovatriptan, almotriptan, zolmitriptan, rizatriptan or a salt thereof as an active ingredient, the method comprising the following steps: (A) adding a buffer to the solvent to adjust the pH of the mixed solution to pH 5.4 to pH 7.4; (B) adding an active ingredient, a film forming agent and an additive to the pH-adjusted mixed solution and stirring it to prepare a final mixed solution; and (C) applying heat to the final mixed solution and drying it to prepare a film in the form of a thin film.

In one embodiment, the solvent may be water, C1-C6 alcohol and a mixed solvent thereof, preferably a 30% to 90% ethanol aqueous solution, and more preferably a 50 to 80% ethanol aqueous solution, but is not limited thereto.

The orally dissolving film formulation of the present invention can be used for the treatment or prevention of migraine.

The orally dissolving film formulation of the present invention can be administered simultaneously or at a time interval with another formulation comprising topiramate as an active ingredient.

In addition, when the orally dissolving film formulation of the present invention comprising 2.5 mg of naratriptan as an active ingredient is administered to a Beagle dog, AUC may be 150 ng·hr/mL to 250 ng·hr/mL, and Cmax may be 30 ng/mL to 60 ng/mL.

The orally dissolving film formulation of the present invention comprising naratriptan is rapidly dissolved during oral dissolution, enabling rapid expression of medicinal effects, and maintaining stability even in an accelerated test for a long period of time (more than 6 months). Therefore, patients with migraine can take it without water, which enhances the convenience of taking it, and it is easy to carry so that they can take it immediately when symptoms occur, so it can be usefully used by patients.

DETAILED DESCRIPTION

Figure 1:
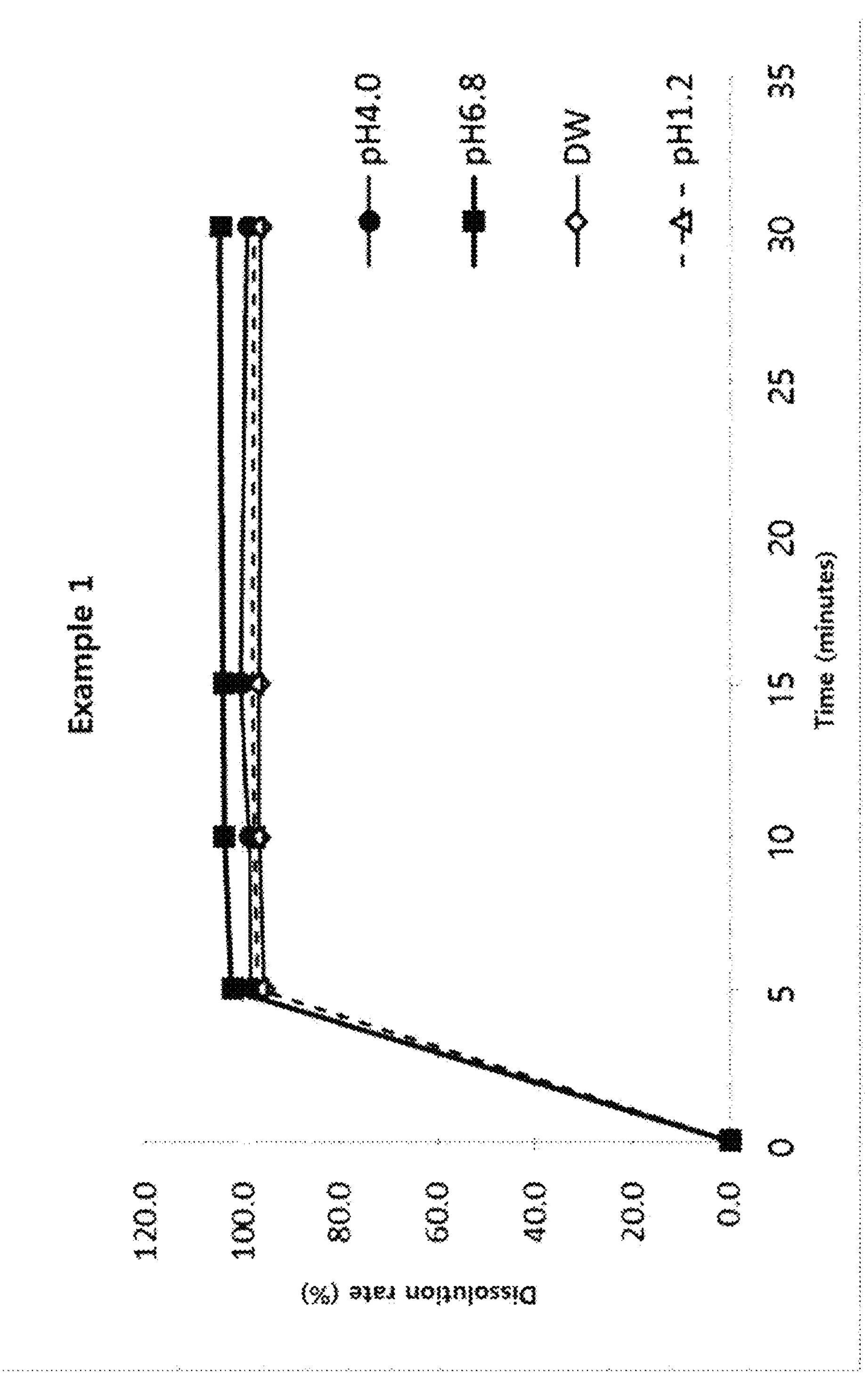
FIG. 1 shows a graph of dissolution rate depending on the pH of the naratriptan film formulation of Example 1.

Hereinafter, with reference to the accompanying drawings, embodiments and examples of the present invention will be described in detail so that those of ordinary skill in the art to which the present invention belongs can easily carry out. However, the present invention may be implemented in various forms and is not limited to the embodiments and examples described herein.

Throughout the present specification, when a certain part "includes" a certain component, it means that other components may be further included, rather than excluding other components, unless otherwise stated.

The present invention relates to an orally dissolving film formulation comprising naratriptan, sumatriptan, eletriptan, frovatriptan, almotriptan, zolmitriptan, rizatriptan or a salt thereof as an active ingredient; and a buffer.

Naratriptan, sumatriptan, eletriptan, frovatriptan, almotriptan, zolmitriptan and rizatriptan as the active ingredient are triptan-based compounds. Solvates or hydrates of triptans as well as triptan-based compounds per se are within the scope of the present invention. The triptan-based compounds are agonists selective for serotonin and can be used as agonists for 5-HT1B1D. The triptan-based compounds are used for migraine, sudden migraine, or cluster migraine, and can be a drug suitable for a film formulation with a small dosage of the drug.

The "salt" may be any acid addition salt or base addition salt that is non-toxic and harmless to the patients and the side effects attributed to the salt do not diminish the beneficial efficacy of the compound of the present invention. Inorganic acids that form suitable salts include hydrochloric acid, phosphoric acid, sulfuric acid, nitric acid, tartaric acid, hydrobromic acid, hydroiodic acid, nitrous acid, or phosphorous acid, and organic acids that form suitable salts include glycolic acid, lactic acid, pyruvic acid, malonic acid, succinic acid, fumaric acid, malic acid, tartaric acid, citric acid, ascorbic acid, maleic acid, benzoic acid, phenylacetic acid, cinnamic acid, salicylic acid, nicotinic acid, tosylic acid, camphorsulfonic acid, naphthoic acid, acetic acid, trifluoroacetic acid, oxalic acid, mandelic acid, propionic acid, citric acid, lactic acid, gluconic acid, galacturonic acid, glutamic acid, glutaric acid, glucuronic acid, aspartic acid, carbonic acid, vanillic acid, benzenesulfonic acid, p-toluenesulfonic acid, or methanesulfonic acid, but are not limited thereto.

The above "orally dissolving film (ODF)" is also referred to as an orally disintegrating film or strip, and refers to a film formulation that can be taken by disintegrating, dissolving, dispersing, and the like in the oral cavity. Such a film formulation is placed on the tongue and dissolved, but can be administered by attaching to the roof of the mouth, sublingually, or the inside of the mouth (buccal). The film formulation according to the present invention has the advantage that it can be taken without water.

The above "pharmacokinetic parameter" refers to a criterion for determining absorption, distribution, metabolism, and excretion of a drug through changes in drug concentration in the body over time. This is a graph showing the relationship between the blood concentration of the administered drug and time. It includes area under the curve (AUC), which is the area enclosed by the drawn curve and the horizontal axis, and maximum plasma concentration (Cmax), which is the maximum concentration or maximum achieved by a drug in a particular compartment or test area of the body after administration of the drug and before the second administration.

The above "buffer" is a pH adjusting agent and includes acids, bases, salts, and the like. It includes, for example, citric acid, sodium citrate, potassium citrate, acetic acid, sodium acetate, malic acid, sodium glutamate, glycine, sodium carbonate, maleic acid, sodium lactate, sodium dihydrogen phosphate, sodium monohydrogen phosphate, potassium dihydrogen phosphate, potassium monohydrogen phosphate or a mixture thereof, and the like, but is not limited thereto. A preferred buffer of the present invention may be citric acid, sodium citrate or a mixture thereof.

In one embodiment, the buffer of the present invention may comprise 0.1 to 2.0% by weight of sodium citrate and 0.01% to 0.1% by weight of citric acid based on the total weight of the film solids.

In the film formulation of the present invention, the content of the total related substances may be less than 3%, preferably less than 2%, and more preferably less than 1% after 6 months during an accelerated stability test.

The film formulation of the present invention may further comprise a film forming agent.

"Film forming agent" refers to a polymer that forms an orally dissolving film formulation, and may be at least one selected from the group consisting of pullulan, sodium alginate, hydroxypropyl cellulose, and hydroxypropyl methyl cellulose. A preferred film forming agent of the present invention may be hydroxypropyl methyl cellulose, but is not limited thereto.

Hereinafter, the present invention will be described in more detail through the examples, but the following examples are for illustrative purposes only and are not intended to limit the scope of the present invention.

Examples 1 to 6

Preparation of Film Formulations of Examples

The film formulations of Examples 1 to 6 were prepared according to the composition shown in Table 1 below as follows.

Purified water and a buffer were put in a preparation container, and naratriptan hydrochloride, an active ingredient, was added, and then the mixture was stirred, and the pH of the solution was adjusted to a range of pH 5.4 to pH 7.4. The remaining additives were put into a preparation container and stirred until a homogeneous solution was obtained, which was used as a film preparation solution.

The prepared film preparation solution was poured onto an OHP film, and cast with a film applicator, and then dried at a temperature of 70° C. or higher, and separated from the OHP film to obtain a film containing naratriptan hydrochloride. The film was cut into one sheet size, and then it was packaged with aluminum wrapping paper.

TABLE 1

| Blending purpose | Name of raw material | Example 1 percentage (%) | Example 2 percentage (%) | Example 3 percentage (%) | Example 4 percentage (%) | Example 5 percentage (%) | Example 6 percentage (%) |
|---|---|---|---|---|---|---|---|
| active ingredient | naratriptan hydrochloride | 7.32 | 7.32 | 7.32 | 7.32 | 7.32 | 7.32 |
| other additives | | 28.95 | 28.95 | 28.95 | 28.95 | 28.95 | 28.95 |
| coloring agent | | | 0.53 | | | | |
| film forming agent | hypromellose E5 | 62.87 | 62.34 | 63.29 | 62.66 | 63.08 | 62.76 |
| buffer | sodium citrate | 0.84 | 0.84 | 0.43 | 1.04 | 0.64 | 0.95 |
| | citric acid | 0.03 | 0.03 | 0.01 | 0.03 | 0.02 | 0.03 |
| percentage (%) of total solids | | 100.00 | 100.00 | 100.00 | 100.00 | 100.00 | 100.00 |

Comparative Examples 1 to 5

Preparation 1 of Film Formulations of Comparative Examples

The film formulations of Comparative Examples 1 to 5 were prepared according to the composition shown in Table 2 below through the same process as in Examples 1 to 6 above.

TABLE 2

| Blending purpose | Name of raw material | Comparative Example 1 percentage (%) | Comparative Example 2 percentage (%) | Comparative Example 3 percentage (%) | Comparative Example 4 percentage (%) | Comparative Example 5 percentage (%) |
|---|---|---|---|---|---|---|
| active ingredient | naratriptan hydrochloride | 7.32 | 7.32 | 7.32 | 7.32 | 7.32 |
| other additives | | 28.95 | 28.95 | 28.95 | 28.95 | 28.95 |
| film forming agent | hypromellose E5 | 63.74 | 58.47 | 58.47 | 62.18 | 62.16 |
| buffer | citric acid | | 5.26 | | | |
| | sodium hydroxide | | | 5.26 | | |
| | sodium dihydrogen phosphate | | | | 0.76 | |
| | sodium monohydrogen phosphate | | | | 0.79 | |
| | potassium | | | | | 0.87 |

TABLE 2-continued

| Blending purpose | Name of raw material | Comparative Example 1 percentage (%) | Comparative Example 2 percentage (%) | Comparative Example 3 percentage (%) | Comparative Example 4 percentage (%) | Comparative Example 5 percentage (%) |
|---|---|---|---|---|---|---|
| | dihydrogen phosphate | | | | | |
| | potassium monohydrogen phosphate | | | | | 0.71 |
| percentage (%) of total solids | | 100.00 | 100.00 | 100.00 | 100.00 | 100.00 |

Comparative Examples 6 to 8

Preparation 2 of Film Formulations of Comparative Examples

The film formulations of Comparative Examples 6 to 8 were prepared according to the composition shown in Table 3 below through the same process as in Examples 1 to 6 above.

TABLE 3

| Blending purpose | Name of raw material | Comparative Example 6 percentage (%) | Comparative Example 7 percentage (%) | Comparative Example 8 percentage (%) |
|---|---|---|---|---|
| active ingredient | naratriptan hydrochloride | 7.32 | 7.32 | 7.32 |
| other additives | | 28.95 | 28.95 | 28.95 |
| film forming agent | hypromellose E5 | 63.74 | 63.74 | 63.74 |
| buffer | citric acid | 0.84 | 0.84 | 0.84 |
| | sodium hydroxide | 0.03 | 0.03 | 0.03 |
| percentage (%) of total solids | | 100.00 | 100.00 | 100.00 |

Experimental Example 1

Dissolution Test of 4 Solutions of Naratriptan Film

A dissolution test was performed on the film formulation of Example 1 under the following conditions and methods. The specific methods and conditions for measuring the dissolution rate were set according to the test method recognized by the Ministry of Food and Drug Safety in Korea as follows.

(1) Preparation of Sample Solution

One sheet of the film prepared in Example 1 was tested using a disc at 50 rotations per minute at 37.0±0.5° C. according to Method 4 of the dissolution test method in the 11th revision of the Korean Pharmacopoeia using 900 mL of pH 1.2, pH 4.0, pH 6.8, and DW as a test solution.

6 mL of the elution solution was taken after 5 minutes, 10 minutes, 15 minutes, and 30 minutes from the beginning of the dissolution test, respectively, and the solution filtered through a 0.45 μm membrane filter was used as a sample solution.

(2) Operating Conditions

Detector: high performance liquid chromatography (measurement wavelength: 224 nm)

Column: C18 (4.6 mm×15 cm, 5 μm)

Mobile phase: isopropyl alcohol: Solution A* (1:9)

*Solution A: 0.6 mL of phosphoric acid is diluted in 900 mL of water, and then trimethylamine is added to this solution to adjust the pH to pH 2.5.

Flow rate: 1.0 mL/min

The results of the dissolution test are shown in Table 4 below and FIG. 1.

TABLE 4

| Test solution | Average dissolution rate (%) (mean ± standard deviation) 5 minutes | 10 minutes | 15 minutes | 30 minutes |
|---|---|---|---|---|
| pH 1.2 | 96.9 | 97.9 | 98.0 | 97.8 |
| pH 4.0 | 98.6 | 99.0 | 100.5 | 99.0 |
| pH 6.8 | 102.3 | 103.9 | 104.1 | 104.8 |
| DW | 95.7 | 96.7 | 96.8 | 96.5 |

As shown in Table 4 above and FIG. 1, it was confirmed that 95% or more of naratriptan was dissolved within 5 minutes. Since it is important that the orally dissolving film is rapidly released, it can be seen that the formulation of Example 1 has excellent effects satisfying the above conditions at all pHs.

Experimental Example 2

Stability Comparison Experiment 1

A stability test was performed using Naramig tablet as a control drug and the film formulations of Examples 1 and 2 in the following manner.

The related substances generated in samples stored for 2 months in an accelerating chamber (a temperature of 40° C., a humidity of 75%, packaged with aluminum quadruple paper) were measured, and the results are shown in Table 5 below and FIG. 2. The operating conditions are as follows.

Detector: high performance liquid chromatography (measurement wavelength: 225 nm)

Column: phenyl group (4.6 mm×15 cm, 5 μm)

Mobile Phase:

| Minute | Solution A ** (%) | Acetonitrile (%) |
|---|---|---|
| 0 | 97 | 3 |
| 35 | 80 | 20 |
| 40 | 80 | 20 |
| 41 | 97 | 3 |
| 51 | 97 | 3 |

** Solution A: 5.75 g of monobasic ammonium phosphate is dissolved in water to make 1 L, and phosphoric acid is added to this solution to adjust the pH to pH 3.00 ± 0.05.

Flow rate: 1.3 mL/min

TABLE 5

| | Initial (%) | Accelerated for 2 months (%) |
|---|---|---|
| Example 1 | 0.07 | 0.15 |
| Example 2 | 0.23 | 0.20 |
| Control drug | 0.31 | 0.32 |

Figure 2:
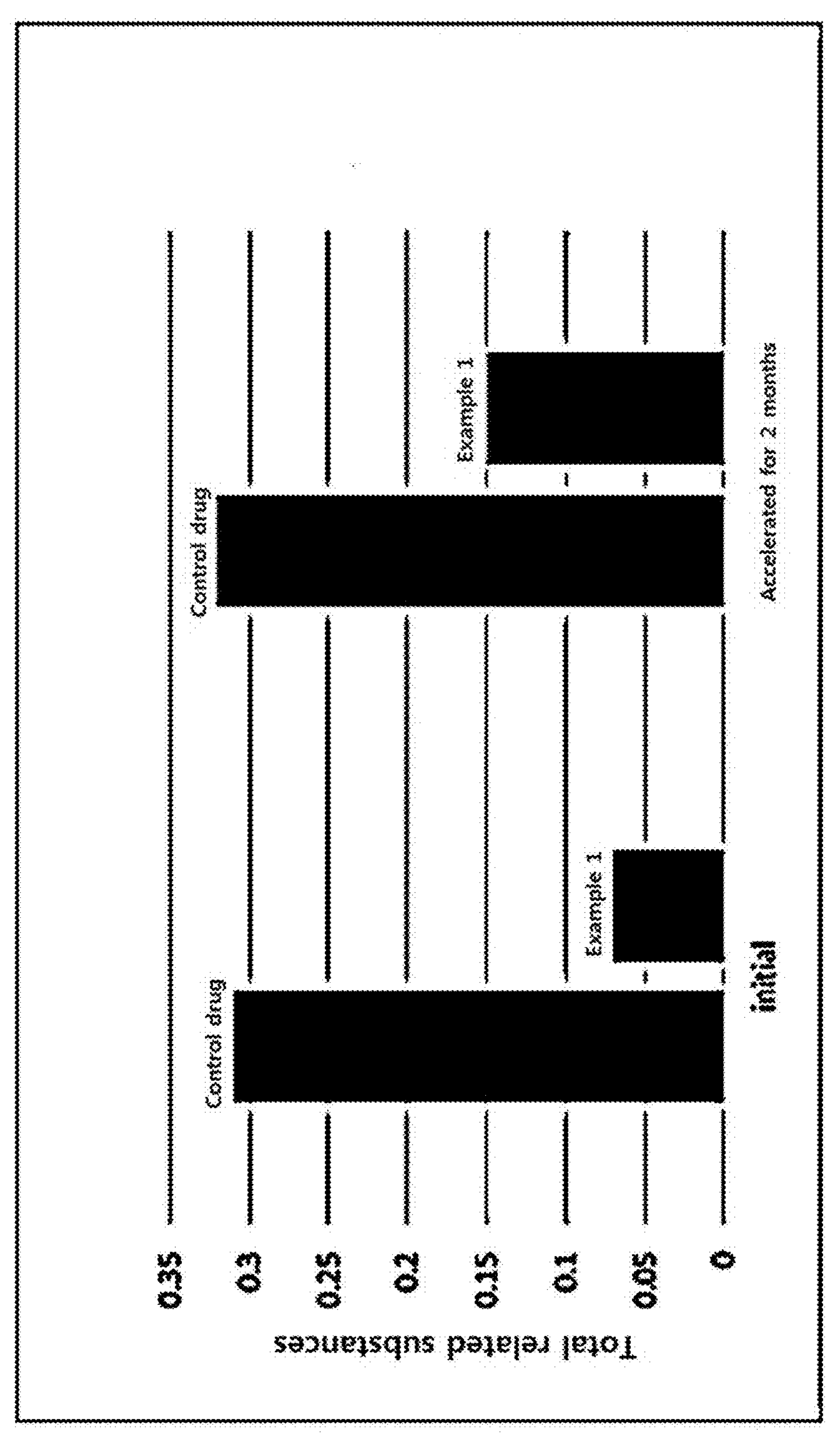
FIG. 2 shows the results of the accelerated test for the control drug (Naramig tablet) and the film formulation of Example 1.

As shown in Table 5 above and FIG. 2, the control drug had an initial amount of related substances of 0.31%, and the film of Example 1 had an initial amount of related substances of 0.07%, which was 4 times less than that of the control drug. In addition, even after the 2-month accelerated experiment, the films of Example 1 and Example 2 had an amount of related substances of 0.2%, which was less than that of the control drug. As a result, it can be seen that the film formulations of Example 1 and Example 2 have exceptionally excellent stability.

Experimental Example 4

Stability Comparison Experiment 2

A stability test was performed on the film formulation of Comparative Example 1 and the film formulation of Example 1 in the following manner.

Figure 3:
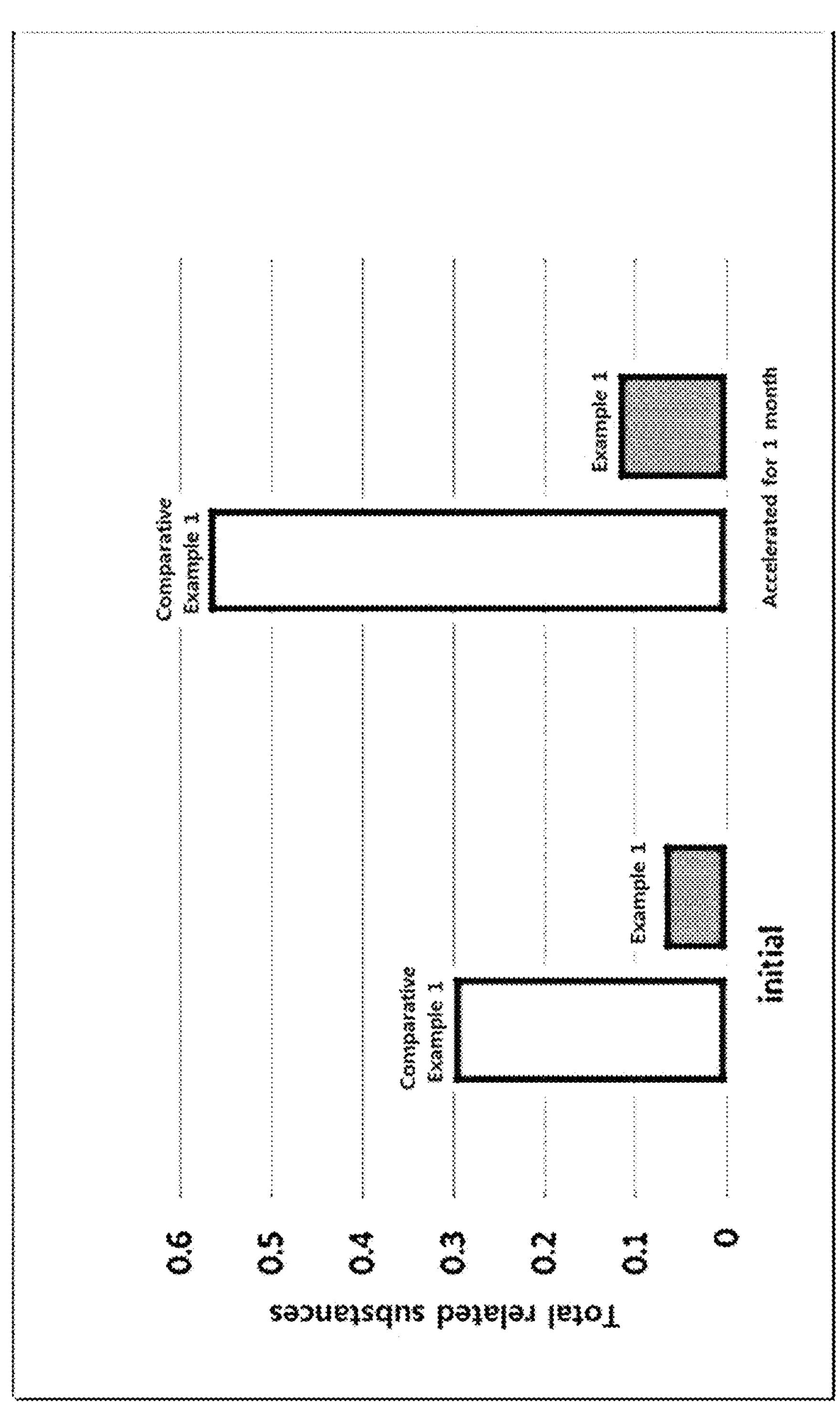
FIG. 3 shows the results of the accelerated test for the film formulations of Example 1 and Comparative Example 1.

The related substances generated in samples stored for 1 month in an accelerating chamber (a temperature of 40° C., a humidity of 75%, packaged with aluminum quadruple paper) were measured, and the results are shown in Table 6 below and FIG. 3. The operating conditions are the same as in Experimental Example 2.

TABLE 6

| | Initial (%) | Accelerated for 1 month (%) |
|---|---|---|
| Example 1 | 0.07 | 0.12 |
| Comparative Example 1 | 0.30 | 0.57 |

Figure 4:
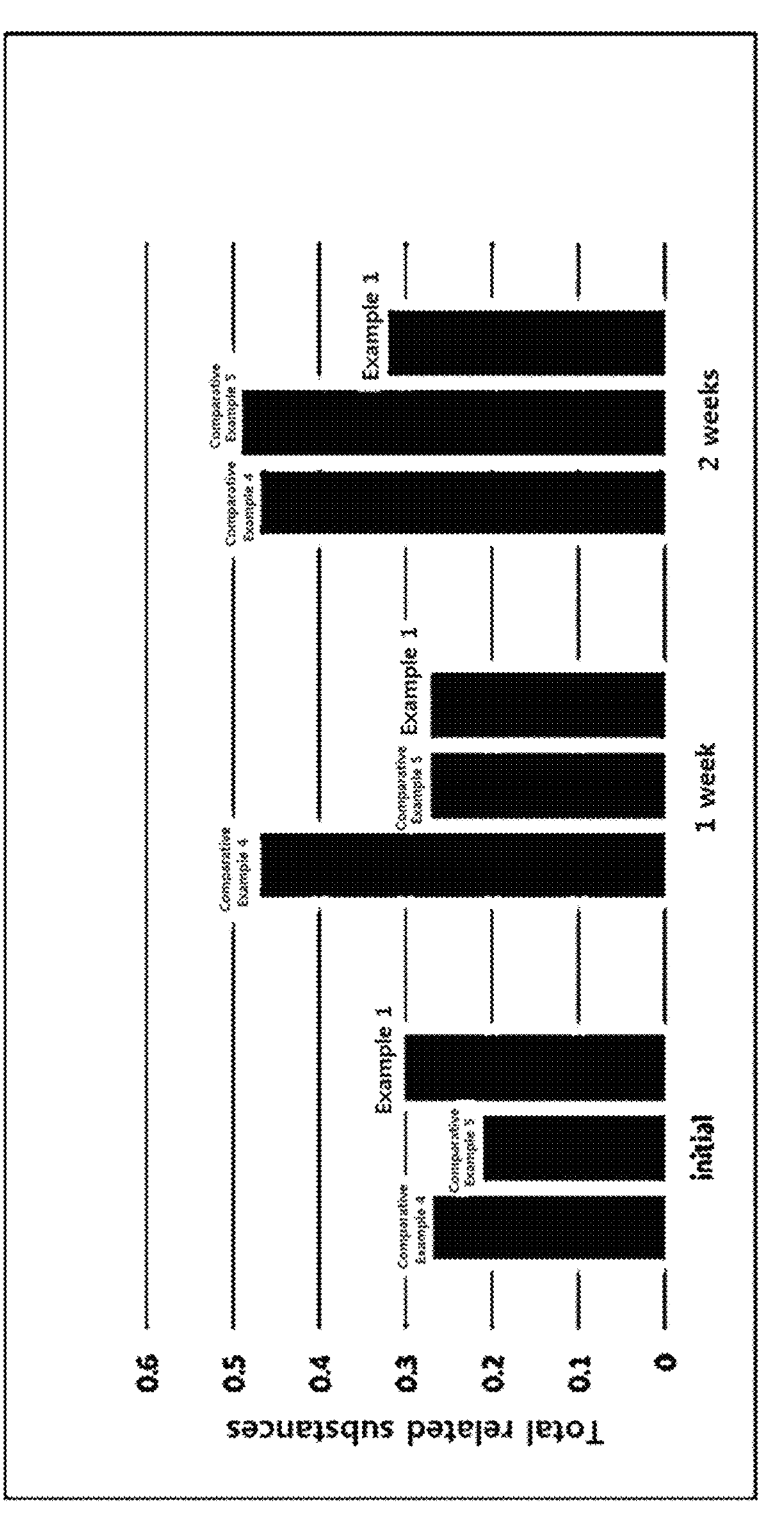
FIG. 4 shows the results of the accelerated test for the film formulations of Example 1 and Comparative Examples 4 and 5 for 2 weeks.

As shown in Table 6 above and FIG. 4, the film of Comparative Example 1 had an initial amount of related substances of 0.30%, and the film of Example 1 had an initial amount of related substances of 0.07%, which was 4 times less than that of the film of Comparative Example 1. In addition, after the 1-month accelerated experiment, the film of Comparative Example 1 had an amount of related substances of 0.57%, and the film of Example 1 had an amount of related substances of 0.12%, which was 4 to 5 times less than that of the film of Comparative Example 1.

As a result, it can be seen that the film formulation of Example 1 having a buffer system has exceptionally excellent stability.

Experimental Example 5

Stability Comparison Experiment 3

A 6-month accelerated test was performed on the film of Comparative Example 2 (acidic), the film of Comparative Example 3 (basic), and the film of Example 1 (citric acid buffer).

The results are shown in Table 7 below.

TABLE 7

| | Example 1 | Comparative Example 2 (acidic) | Comparative Example 3 (basic) |
|---|---|---|---|
| pH | 6.6 | 1.2 | 10.0 |
| Initial | 0.07 | 0.06 | 0.11 |
| accelerated for 1 month | 0.12 | 1.74 | 0.66 |
| accelerated for 3 months | 0.20 | 2.02 | 1.74 |
| accelerated for 6 months | 0.39 | 3.58 | 4.24 |

As shown in Table 7 above, it was confirmed that the film of Example 1 had a very small amount of related substances compared to the films of Comparative Examples 2 and 3 and had exceptionally excellent stability. In particular, after the 6-month accelerated experiment, it can be seen that the film of Example 1 had an amount of related substances of 0.39%, whereas the films of Comparative Examples 2 and 3 had an amount of related substances of 3.58% and 4.24%, respectively, which were about 10 times more than that of the film of Example 1.

As a result, it was confirmed that the film of Example 1 using a neutral buffer had excellent stability.

Experimental Example 6

Stability Comparison Experiment 4

An accelerated test was performed on the film of Comparative Example 4 (sodium dihydrogen phosphate ($NaH2PO4$) and sodium monohydrogen phosphate ($Na2HPO4$)) and the film of Comparative Example 5 (potassium dihydrogen phosphate ($KH2PO4$) and potassium monohydrogen phosphate ($K2HPO4$)), and the film of Example 2 (citric acid buffer).

Figure 5:
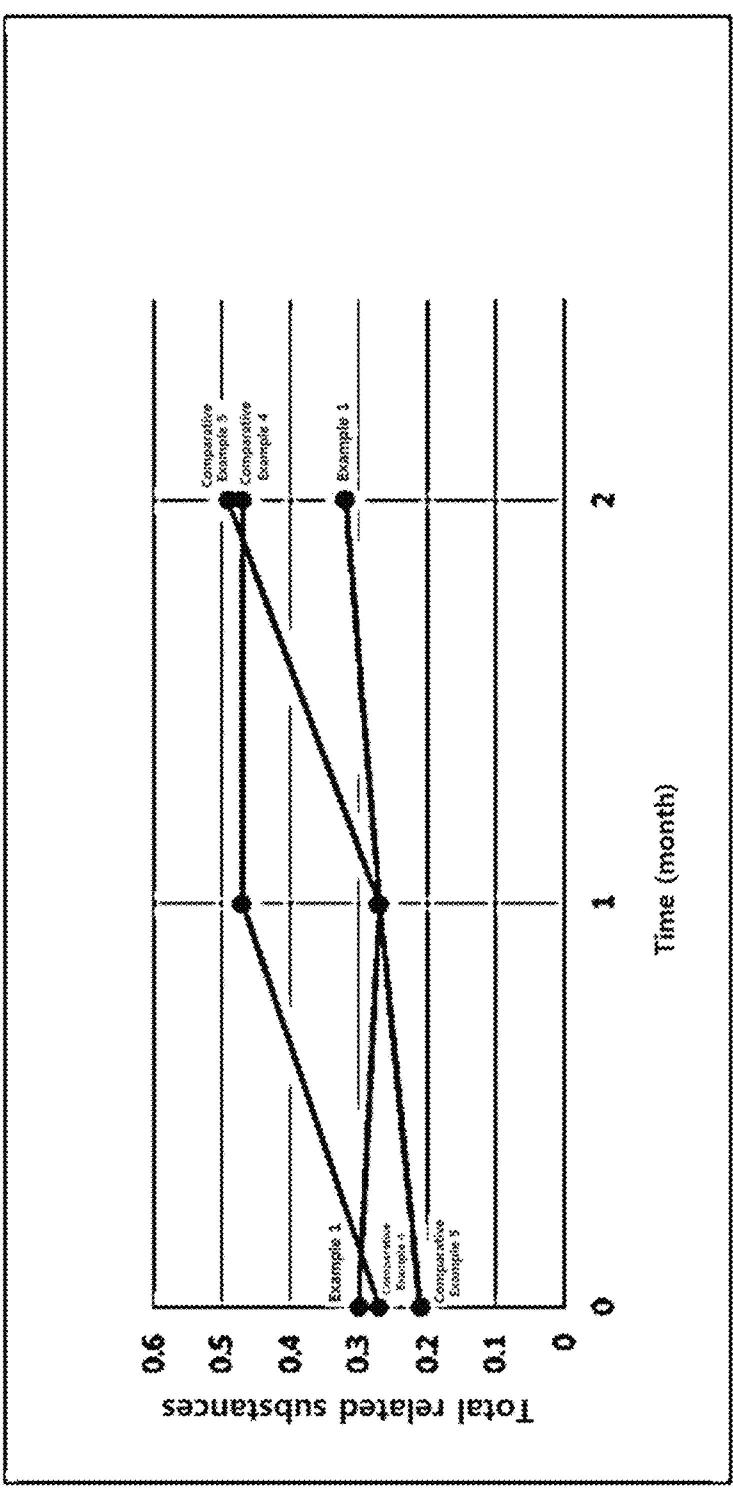
FIG. 5 shows the results of the accelerated test for the film formulations of Example 1 and Comparative Examples 4 and 5 for 2 months.

As a result, as shown in FIGS. 4 and 5, it was confirmed that the film of Example 1 had excellent stability compared to the films of Comparative Examples 4 and 5.

Experimental Example 7

Comparison of Shape Depending on Concentration of Buffer

Figure 6:
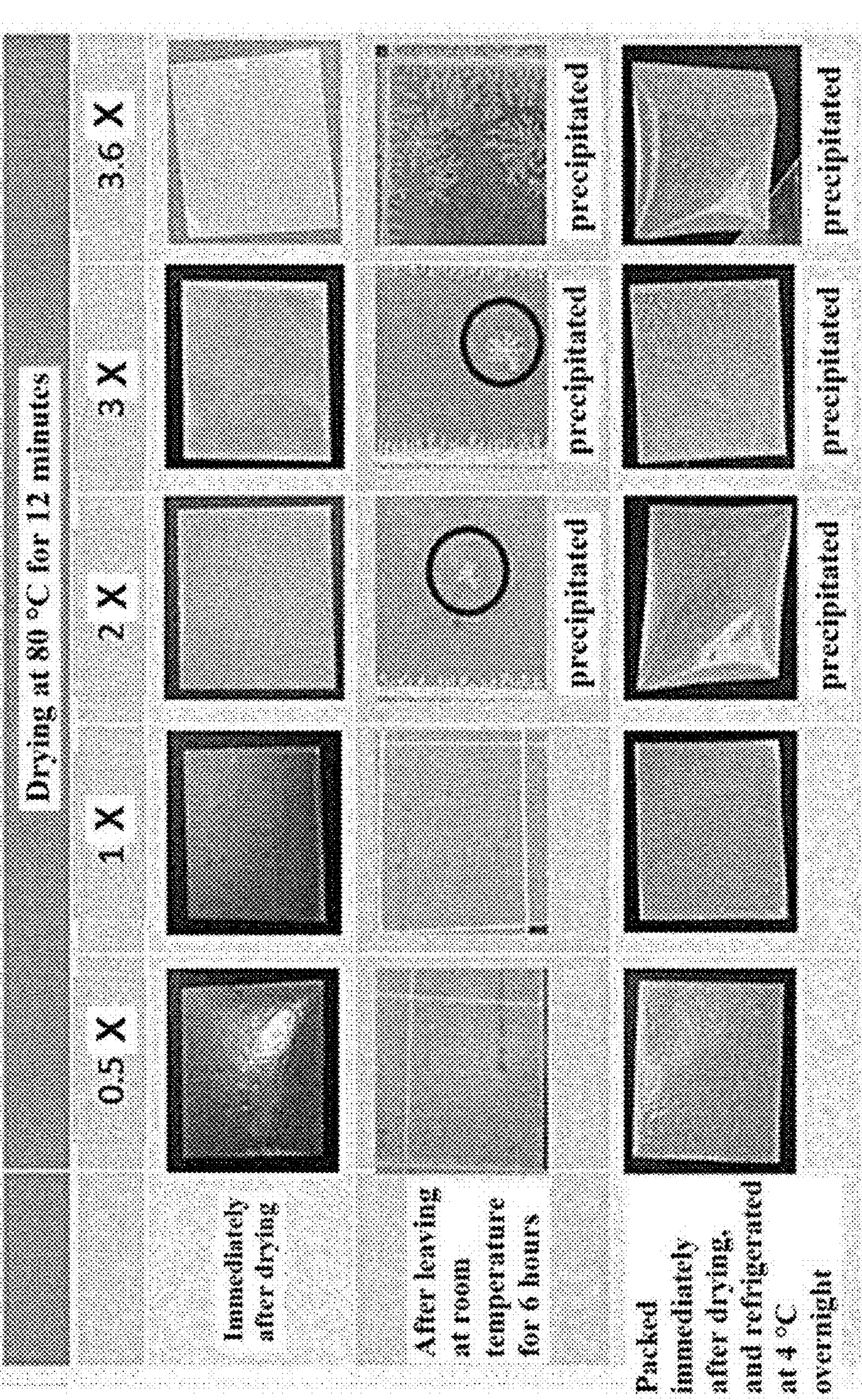
FIGS. 6 to 9 show the shape of the film after drying the film.
Figure 7:
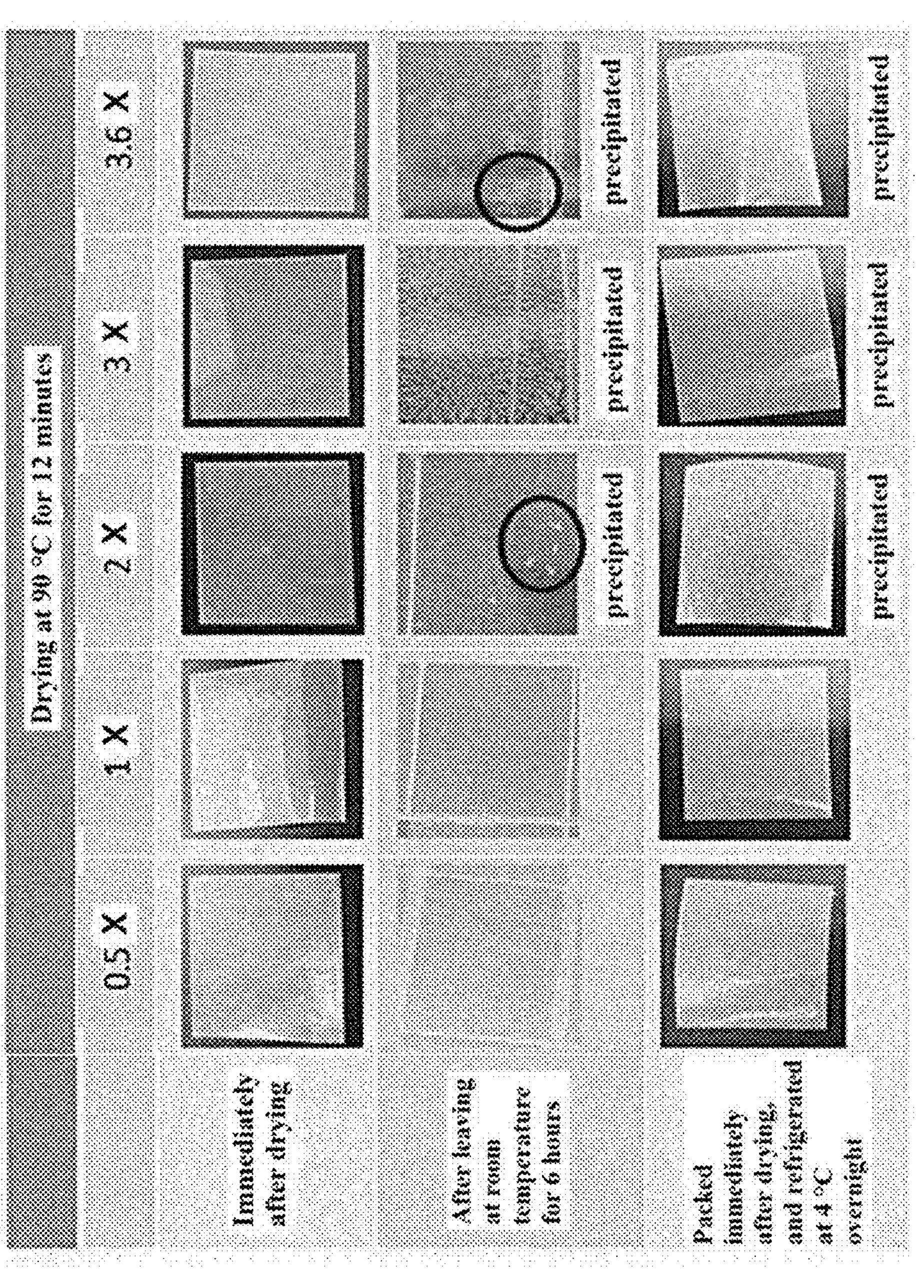

The film formulation of Example 1 was prepared at 0.5, 1, 2, 3 and 3.6 times the concentration of the buffer and then dried at 80° C. and 90° C. for 12 minutes, respectively, and the shape of the film was observed (1 time=0.05 M). The results are shown in Tables 8 and 9 below and FIGS. 6 and 7.

TABLE 8

| Drying at 80° C. for 12 minutes | | | | | |
|---|---|---|---|---|---|
| Concentration of buffer | 0.5 X | 1 X | 2 X | 3 X | 3.6 X |
| Immediately after drying | — | — | | | |
| After leaving at room temperature for 6 hours | — | — | precipitated | precipitated | precipitated |
| Packed immediately after drying, and refrigerated at 4° C. overnight | — | — | precipitated | precipitated | precipitated |

TABLE 9

| Drying at 90° C. for 12 minutes | | | | | |
|---|---|---|---|---|---|
| Concentration of buffer | 0.5 X | 1 X | 2 X | 3 X | 3.6 X |
| Immediately after drying | — | — | — | — | — |
| After leaving at room temperature for 6 hours | — | — | precipitated | precipitated | precipitated |
| Packed immediately after drying, and refrigerated at 4° C. overnight | — | — | precipitated | precipitated | precipitated |

As shown in the tables above, it was confirmed that crystals were precipitated when the concentration of the buffer was twice or more.

In addition, the film formulation of Example 1 was prepared at 1.25, 1.5 and 1.75 times the concentration of the buffer and then dried at 80° C. and 90° C. for 12 minutes, respectively, and the shape of the film was observed.

Figure 8:
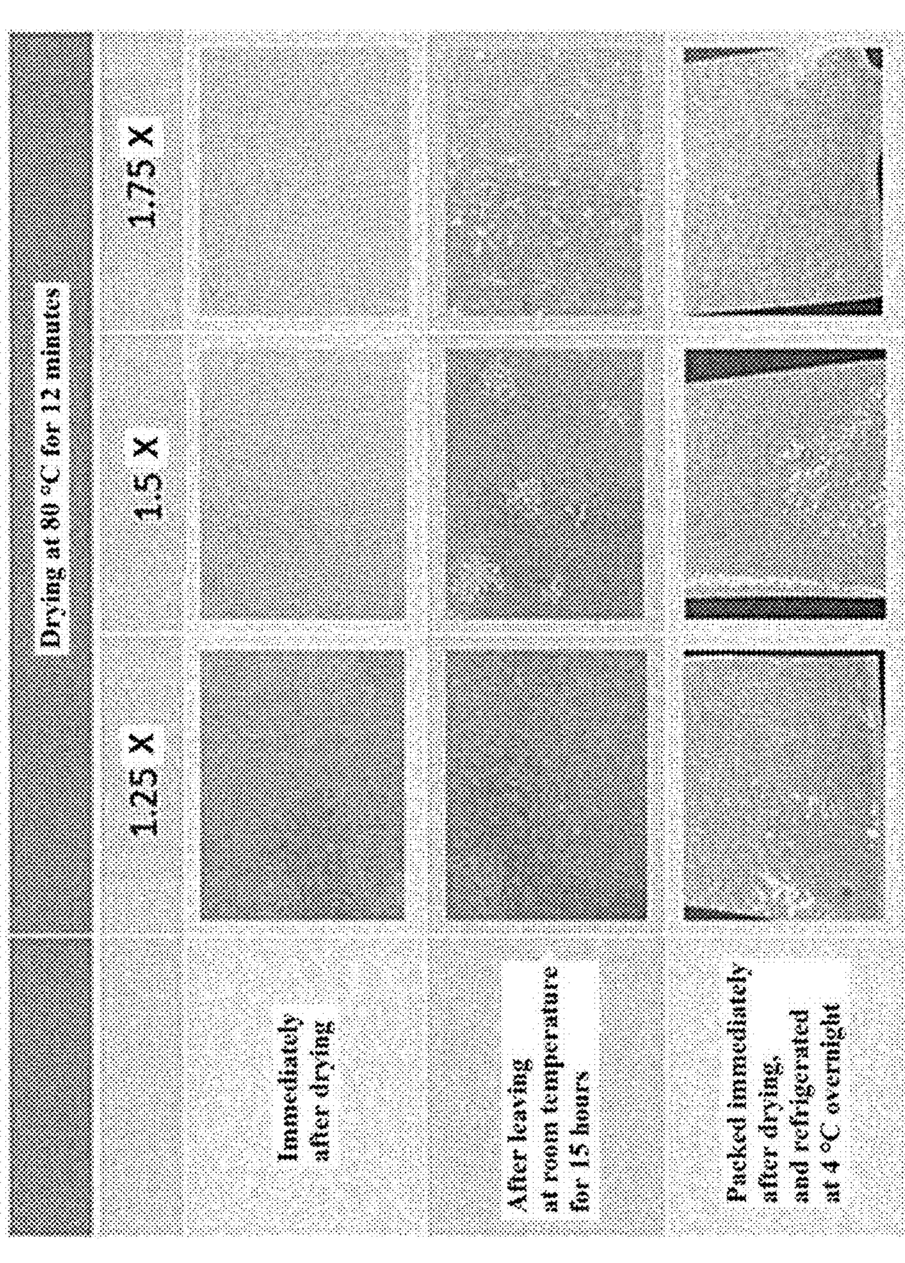
Figure 9:
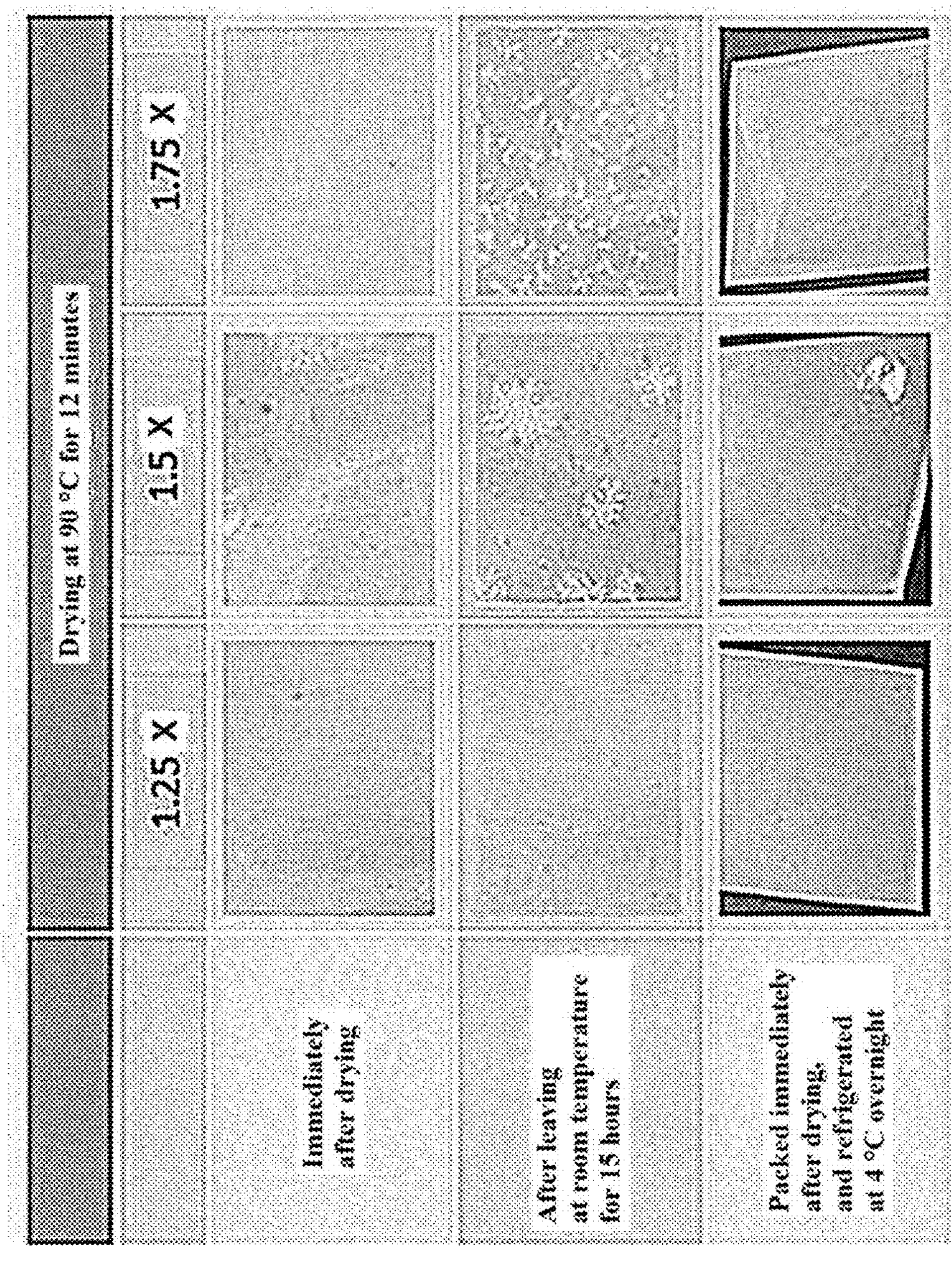

The results are shown in Tables 10 and 11 below and FIGS. 8 and 9.

TABLE 10

| | Drying at 80° C. for 12 minutes | | |
|---|---|---|---|
| | 1.25 X | 1.5 X | 1.75 X |
| Immediately after drying | — | — | — |
| After leaving at room temperature for 6 hours | — | precipitated | precipitated |
| Packed immediately after drying, and refrigerated at 4° C. overnight | — | — | precipitated |

TABLE 11

| | Drying at 90° C. for 12 minutes | | |
|---|---|---|---|
| | 1.25 X | 1.5 X | 1.75 X |
| Immediately after drying | — | — | — |
| After leaving at room temperature for 6 hours | — | precipitated | precipitated |
| Packed immediately after drying, and refrigerated at 4° C. overnight | — | — | precipitated |

As shown in the tables above, it was confirmed that crystals were not precipitated until the concentration of the buffer was 1.25 times.

Experimental Example 8

Stability Comparison Experiment Depending on Concentration of Buffer

The film formulation of Example 1 was prepared at 0.75, 1 and 1.25 times the concentration of the buffer, and then a stability test was performed.

Figure 10:
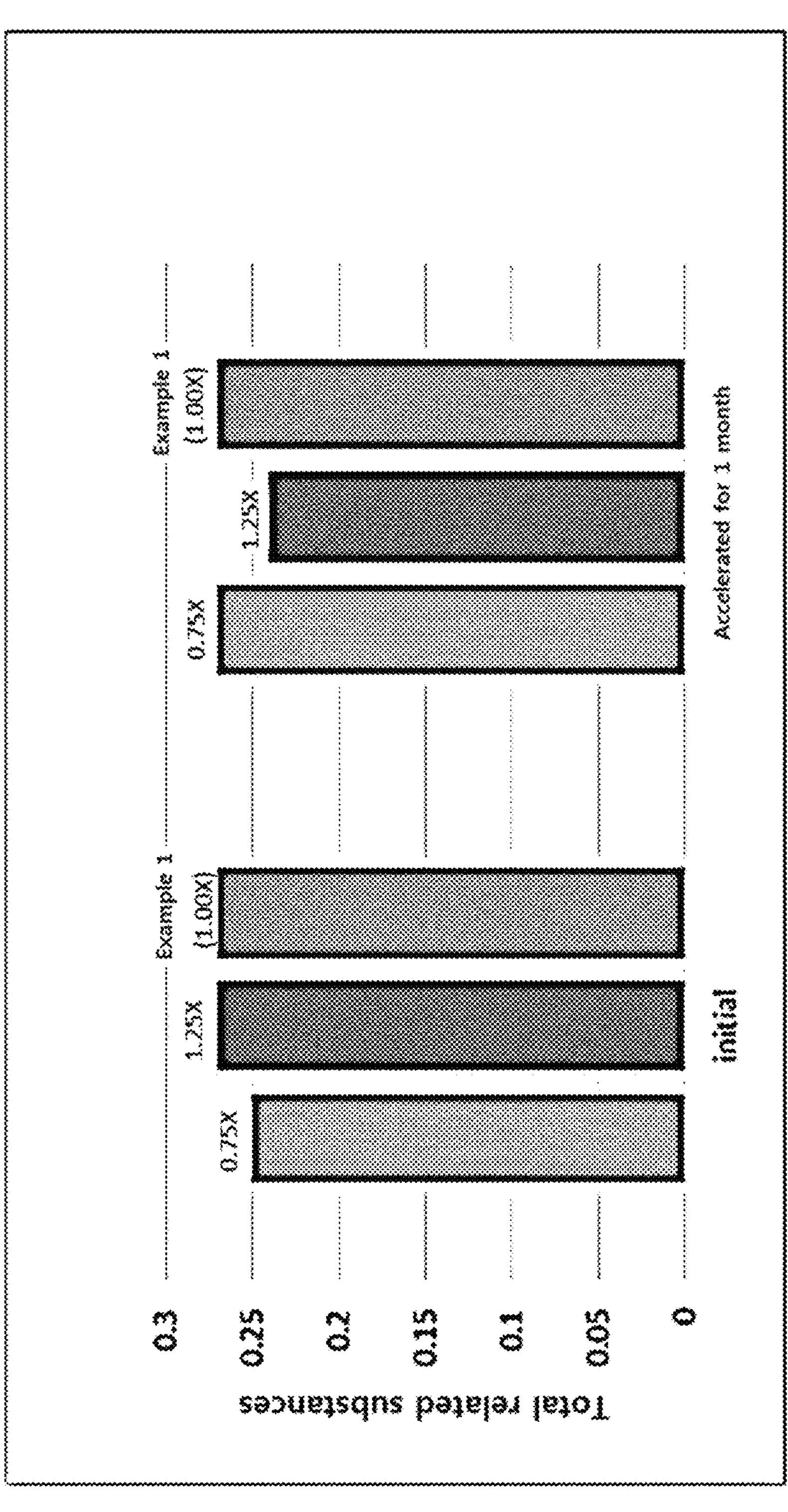
FIG. 10 shows the results of the accelerated test depending on the concentration of a buffer.
Figure 11:
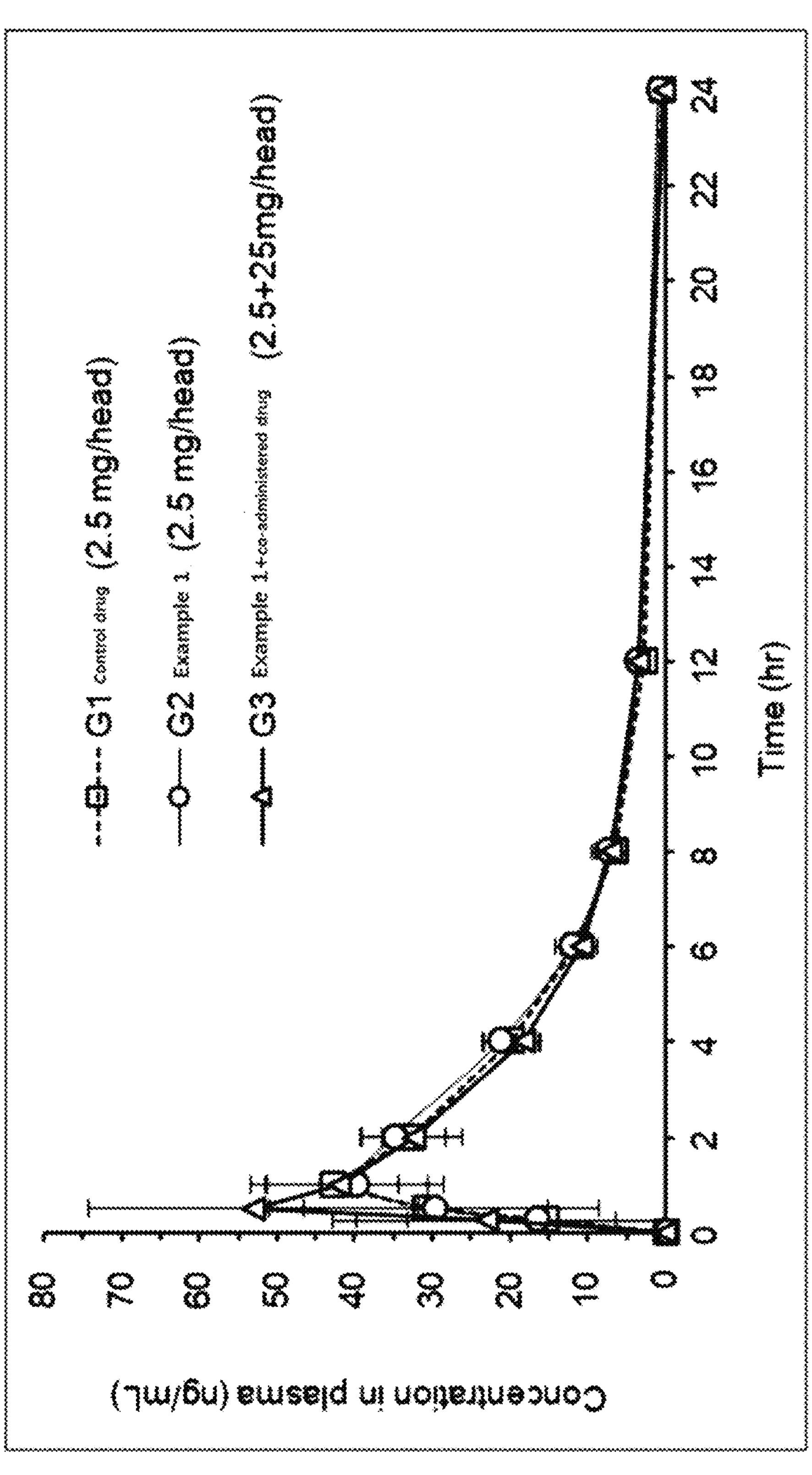
FIG. 11 shows the results of animal experiments on naratriptan films.

As a result, as shown in FIG. 10, it was confirmed that there was no difference in stability for each concentration, and it can be seen that the stability was excellent until the concentration of the buffer was 1.25 times.

Experimental Example 9

Animal Experiment on Naratriptan Film

An animal experiment was performed using Naramig tablet as a control drug, Topamax tablet as a co-administered drug, and the film formulation of Example 1 in the following manner.

In G1, one tablet of the control drug (Naramig tablet) was administered to a Beagle dog, and in G2, one sheet of the film of Example 1 was administered to a Beagle dog, and in G3, one sheet of the film of Example 1 and one tablet of Topamax tablet were administered to a Beagle dog in order to confirm the interaction between naratriptan and topiramate drugs.

Blood was collected at 0 minute, 15 minutes, 30 minutes, 1 hour, 2 hours, 3 hours, 4 hours, 5 hours, 6 hours, 8 hours, 12 hours, and 24 hours after the start of administration to the Beagle dog, and the plasma concentration of the drug was measured.

The plasma concentration of the drug was measured and the pharmacokinetic parameters were calculated, and the results are shown in Table 12 below.

TABLE 12

| | AUC (ng · hr/mL) | Cmax (ng/mL) | Tmax (hr) |
|---|---|---|---|
| G1 (control drug) | 189.00 | 46.10 | 0.80 |
| G2 (Example 1) | 213.90 | 44.20 | 0.67 |
| G3 (Example 1 + co-administered drug) | 194.80 | 54.50 | 0.67 |

As shown in Table 12 above, AUC, Tmax, and Cmax of the G1 group and the G2 group were evaluated to be equivalent. Therefore, it can be seen that the duration of drug effect, maximum concentration, and bioavailability of the control drug and the formulation of Example 1 are equivalent. In addition, in the case of the G1 group (Example 1) and the G3 group (Example 1+co-administered drug), AUC, Tmax, and Cmax were evaluated to be equivalent. The co-administration of the orally dissolving film was evaluated to be equivalent to the single administration as it was suitable within the confidence interval of 80% to 125%, and it was confirmed that there was no interaction between naratriptan and topiramate drugs.

What is claimed is:

1. An orally dissolving film formulation comprising:

a) naratriptan or a salt thereof as an active ingredient; and b) a mixture of citric acid and sodium citrate as a buffer, wherein the buffer comprises 0.42 to 1.05% by weight of sodium citrate and 0.015 to 0.038% by weight of citric acid based on the total weight of the film solid.

2. The orally dissolving film formulation according to claim 1, wherein the active ingredient is dissolved by 85% or more within 5 minutes during a dissolution test.

3. The orally dissolving film formulation according to claim 2, wherein the active ingredient is dissolved by 90% or more within 5 minutes during a dissolution test.

4. The orally dissolving film formulation according to claim 1, wherein the amount of related substances is less than 3% by weight after 6 months of accelerated stability testing.

5. The orally dissolving film formulation according to claim 4, wherein the amount of related substances is less than 2% by weight after 6 months of accelerated stability testing.

6. The orally dissolving film formulation according to claim 1, wherein the orally dissolving film formulation further comprises a film forming agent.

7. The orally dissolving film formulation according to claim 6, wherein the film forming agent is pullulan, sodium alginate, hydroxypropyl cellulose, hydroxypropyl methyl cellulose or a mixture thereof.

8. The orally dissolving film formulation according to claim 7, wherein the film forming agent is hydroxypropyl methyl cellulose.

9. A method for preparing the orally dissolving film formulation of claim 1, the method comprising the following steps:

(A) adding a buffer to a solvent to adjust the pH of mixed solution to pH 5.4 to pH 7.4;

(B) adding an active ingredient, a film forming agent, and an additive to the pH-adjusted mixed solution and stirring the pH-adjusted mixed solution to prepare a final mixed solution; and (C) applying heat to the final mixed solution and drying the final mixed solution to prepare a film in the form of a thin film.

10. The method according to claim 9, wherein the solvent is water, C1-C6 alcohol, or any combination thereof.

11. A method of treating or preventing migraine comprising administering the orally dissolving film formulation of claim 1 to a subject in need thereof.

12. The method according to claim 11, wherein the orally dissolving film formulation is administered simultaneously with or at a time interval relative to another formulation comprising topiramate as an active ingredient.

13. The orally dissolving film formulation according to claim 1, wherein when the orally dissolving film formulation comprising 2.5 mg of naratriptan as an active ingredient is administered to a Beagle dog, AUC is 150 ng·hr/mL to 250 ng·hr/mL, and Cmax is 30 ng/ml to 60 ng/mL.

* * * * *